(12) United States Patent
Bollu et al.

(10) Patent No.: US 11,066,368 B2
(45) Date of Patent: Jul. 20, 2021

(54) PROCESS FOR THE PREPARATION AND PARTICLE SIZE REDUCTION OF PIRFENIDONE

(71) Applicant: Laurus Labs Limited, Hyderabad (IN)

(72) Inventors: Ravindra Babu Bollu, Hyderabad (IN); Venkata Pramod Kumar Mandadapu, Hyderabad (IN); Venkata Sunil Kumar Indukuri, Hyderabad (IN); Satyanarayana Chava, Hyderabad (IN); Tirumala Rao Galla, Hyderabad (IN); Jagadeeswara Rao Dadi, Hyderabad (IN); Uma Maheswer Rao Vasireddi, Hyderabad (IN)

(73) Assignee: Laurus Labs Limited, Hyderabad (IN)

(*) Notice: Subject to any disclaimer, the term of this patent is extended or adjusted under 35 U.S.C. 154(b) by 0 days.

(21) Appl. No.: 16/032,210

(22) Filed: Jul. 11, 2018

(65) Prior Publication Data

US 2018/0334434 A1 Nov. 22, 2018

Related U.S. Application Data

(63) Continuation-in-part of application No. PCT/IB2017/050141, filed on Jan. 12, 2017.

(30) Foreign Application Priority Data

Jan. 14, 2016 (IN) .............................. 201641001390
Dec. 11, 2017 (IN) .............................. 201741044403

(51) Int. Cl.
C07D 213/64 (2006.01)

(52) U.S. Cl.
CPC ................... C07D 213/64 (2013.01)

(58) Field of Classification Search
CPC .................................................. C07D 213/64
See application file for complete search history.

(56) References Cited

U.S. PATENT DOCUMENTS

| 3,839,346 A | 10/1974 | Gadekar |
| 8,519,140 B2 | 8/2013 | Radhakrishnan et al. |
| 2012/0016133 A1 | 1/2012 | Pyles et al. |
| 2012/0192861 A1* | 8/2012 | Surber ................. A61K 9/0078 128/200.16 |
| 2012/0329888 A1* | 12/2012 | Engel .................. B01F 17/0007 516/194 |
| 2013/0119174 A1* | 5/2013 | Lelas ...................... B02C 13/20 241/187 |
| 2014/0370065 A1* | 12/2014 | Ahlnas ................... A01N 59/00 424/405 |

FOREIGN PATENT DOCUMENTS

| CA | 2764043 A1 | 12/2010 |
| CN | 100396669 C | 6/2008 |
| CN | 101891676 A | 11/2010 |
| CN | 102558040 A | 7/2012 |
| EP | 2440543 A2 | 4/2012 |
| WO | WO-2002/085858 A1 | 10/2002 |
| WO | WO-2003/014087 A1 | 2/2003 |
| WO | WO-2008147170 A1 | 12/2008 |
| WO | WO-2010141600 A2 | 12/2010 |
| WO | WO-2016/122420 A1 | 8/2016 |

OTHER PUBLICATIONS

Loh et al 2015 Asian J Pharm Sciences 10 pp. 255-274, "Overview of milling techniques for improving the solubility of poorly water-soluble drugs.".*
Patel et al., ("An overview of size reduction technologies in the field of pharmaceutical manufacturing," in Asian Journal of Pharmaceutics-Oct.-Dec. 2008).*
International Search Report for PCT/IB2017/050141 dated Mar. 30, 2017.

* cited by examiner

Primary Examiner — Blessing M Fubara
(74) Attorney, Agent, or Firm — Blank Rome LLP

(57) ABSTRACT

The present invention relates to an improved process for the preparation of pure pirfenidone having a particular particle size distribution, a crystalline form of pirfenidone, and pharmaceutical compositions thereof, as well as methods for particle size reduction of pirfenidone, and methods for particle size reduction of pirfenidone by wet milling techniques using colloid mill, ultrasonicator, or high speed homogenizer devices.

30 Claims, 2 Drawing Sheets

PROCESS FOR THE PREPARATION AND PARTICLE SIZE REDUCTION OF PIRFENIDONE

CROSS-REFERENCE TO RELATED APPLICATIONS

This application is a continuation-in-part application based on and claims the benefit of International Application PCT/IB2017/050141, filed on Jan. 12, 2017 (published on Jul. 20, 2017), which is itself based on and claims the benefit of Indian Provisional Application No. 201641001390, filed on Jan. 14, 2016, entitled "An improved process for the preparation of pirfenidone." This application is also based on and claims the benefit of Indian Provisional Application No. 201741044403, filed on Dec. 11, 2017, entitled "Method for particle size reduction of pirfenidone." The content of each of the above-referenced applications are incorporated by reference herein.

FIELD OF THE INVENTION

The present invention relates to an improved process for the preparation of pure pirfenidone. The present invention also relates to a crystalline form of pirfenidone and is pharmaceutical composition thereof.

The present invention also generally relates to processes for particle size reduction of pirfenidone by wet milling techniques.

BACKGROUND OF THE INVENTION

Pirfenidone is an anti-fibrotic drug for the treatment of idiopathic pulmonary fibrosis (IPF). It works by reducing lung fibrosis through down regulation of the production of growth factors and procollagens I and II. Pirfenidone was approved by USFDA for the treatment of idiopathic pulmonary fibrosis on Oct. 15, 2014. Pirfenidone is chemically known as 5-methyl-1-phenyl-2-1(H)-pyridone and represented by the following structural formula (I)

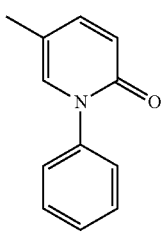

Formula (I)

Idiopathic pulmonary fibrosis (IPF) is a rare disease of unknown etiology that is characterized by progressive fibrosis of the interstitium of the lung, leading to decreasing lung volume and progressive pulmonary insufficiency.

The process for the preparation of pirfenidone was first disclosed in U.S. Pat. No. 3,839,346. The disclosed process involves reaction of 5-methyl-2-(1H)-pyridone with iodobenzene in presence of anhydrous potassium carbonate and zinc precipitated copper powder to get pirfenidone.

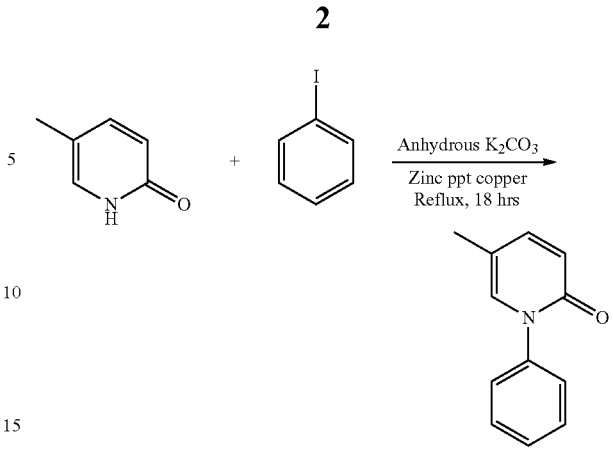

PCT publication WO 2002/085858 disclosed the purification process for pirfenidone, which involves dissolution of pirfenidone in 5% aqueous acetic acid at 90° C. and adding 25% aqueous sodium hydroxide followed by isolating pure pirfenidone.

PCT publication WO 2003/014087 disclosed an improved process of pirfenidone, which involves the reaction of 5-methyl-2(1H)-pyridinone with bromobenzene in the presence of cuprous oxide and potassium carbonate at 156° C. followed by isolation and purification of pirfenidone by acid-base treatment.

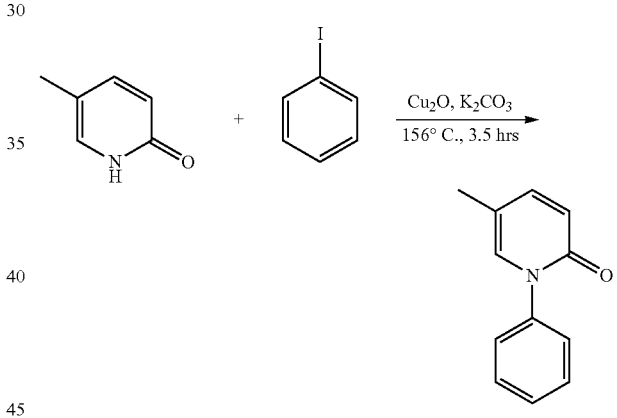

U.S. Pat. No. 8,519,140 ("the '140 patent") disclosed an improved process for the preparation of pure pirfenidone, which involves the reaction of 5-methyl-2(1H)-pyridinone with bromobenzene having less than 0.15% by weight dibromobenzene in presence of a cuprous oxide, potassium carbonate in dimethylsulfoxide followed by crystallization of obtained pirfenidone by acid-base treatment. According to this patent, purity of dibromobenzene is important, as amount of dibromobenzene impurity in the bromobenzene can lead to dimer type byproducts, which complicate the purification of pirfenidone and difficult to remove from final pirfenidone. Further states that bromobenzene with less that 0.15% of dibromobenzene is not readily available and moreover expensive when compared with the regular bromobenzene.

PCT publication WO2016/122420 disclosed an improved process for the preparation of pirfenidone, which involves the reaction of 5-methyl-2-pyridone with low quantity of bromobenzene in a low quantity of solvent, in presence of copper catalyst such as Cu(I) or Cu(ll) salts and a base. This publication further disclosed the purification of pirfenidone by formation of pirfenidone acid adducts with strong acids followed by recovery of pirfenidone from the adduct.

Further number of patents/publications such as CN100396669 C, WO2008/147170, CN101891676 A and CN102558040 disclosed the improved process for the preparation of pirfenidone, which involves similar chemistry i.e., reaction of 5-methyl-2-(1H)-pyridinone with iodo or bromobenzene in presence of copper catalyst and a base in a suitable solvent.

Hence there is a need in the art to develop an improved process for the preparation of pure pirfenidone with high product yield and purity with commercially available bromobenzene having dibromobenzene content about 0.2% or more, in a convenient and cost efficient manner and on a commercial scale.

U.S. Pat. No. 3,839,346 remains silent about particle size of obtained pirfenidone.

U.S. Pat. No. 8,519,140 ("the '140 patent") disclosed an improved process for the preparation of pirfenidone and the obtained pirfenidone was milled through a loop mill in order to reduce the particle size to less than 150 µm.

In pharmaceutical industry, particle characterization of powder materials has become one of the crucial aspects in drug product development and quality control of solid oral dosage forms. The particle size distribution (PSD) of the drug substance may have significant effects on final drug product performance (e.g., dissolution, bioavailability, content uniformity, stability, etc.). Furthermore, the PSDs of both drug substance and excipients can affect drug product manufacturability (e.g., flowability, blend uniformity, compactibility, etc.), which, ultimately, can impact safety, efficacy, and quality of the drug product. The PSDs of pharmaceutical powders have profound influence on almost every step of manufacturing processes for solid oral dosage forms, including pre-mixing/mixing, granulation, drying, milling, blending, coating, encapsulation, and compression. Therefore, the impact of particle sizes of pharmaceutical powders on drug product manufacturability and performance should be evaluated at different pharmaceutical development phases for each specific drug application.

The present inventors have found that by performing safety studies pirfenidone is a dust explosive, shock sensitive and having a very low minimum Ignition energy. Based on the studies, it was observed that pirfenidone is a $St_{2H}$ class (violent explosion nature) with sparks and fumes and having very low minimum ignition energy of 1.7 mJ, which indicates the material can ignite even at low ignition energy.

Particle size reduction process disclosed under the '140 Patent involves loop mill technique. A loop mill grinds materials by using a high speed jet of compressed air or inert gas in dry state to impact particles into each other. Dry milling process used in the loop mill particle size reduction always generates energetic particles that generate thermal energy which generally leads to explosion or burnings.

Based on these studies, the present inventors have realized that known dry mill technique is not appropriate selection for a material that has aforementioned drawbacks, for instance pirfenidone to avoid explosion due to static charge dissipation (*Hammer Milling and Jet Milling Fundamentals Gary Liu, P. E. June,* 2017).

Hence there is a need in the art to develop an alternative particle size reduction technique, which is suitable for sensitive materials that having a nature of dust explosive, shock sensitive and low ignition energy. Therefore the present invention provides alternative milling techniques in order to overcome the aforementioned drawbacks. More specifically, the present invention provides wet mill techniques like colloid mill, ultra-sonication and high speed homogenizer techniques to reduce the particle size distribution of pirfenidone to below about 500 µm.

SUMMARY OF THE INVENTION

Accordingly the present invention provides an improved process for the preparation of pure pirfenidone. More specifically, provides an improved process for pirfenidone which comprise of reacting the 5-methyl-1H-pyridin-2-one of formula-II with bromobenznene, wherein the bromobenzene contain about 0.2% or more by weight dibromobenzene.

In one embodiment, the present invention provides an improved process for the preparation of pirfenidone of formula (I),

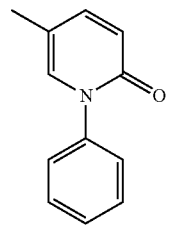

Formula (I)

which comprises the reaction of 5-methyl-1H-pyridin-2-one of formula (II)

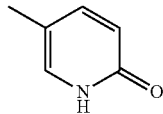

Formula (II)

with bromobenzene of formula (III)

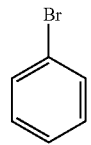

Formula (III)

in the presence of a suitable copper catalyst and a base in a suitable organic solvent under sufficient conditions to provide pirfenidone, wherein the bromobenzene contain about 0.2% or more by weight dibromobenzene.

In another embodiment, the present invention provides an improved process for the preparation of pirfenidone, which comprises the reaction of 5-methyl-1H-pyridin-2-one with bromobenzene in presence of copper chloride and potassium carbonate in dimethylformamide under sufficient conditions to provide pirfenidone, wherein the bromobenzene contain about 0.2% or more by weight dibromobenzene.

In another embodiment the present invention provides crystalline pirfenidone characterized by its Powder X-ray diffractogram having one or more peaks at about 8.76, 14.22, 14.90, 18.36, 18.72, 19.86, 20.90, 21.92, 22.52, 22.86, 24.22, 26.96, 27.20, 28.16, 28.80, 29.50, 30.20, 31.42, 32.32, 37.02, 39.40 and 43.38±0.2°2θ or by a powder X-Ray diffraction (PXRD) pattern substantially in accordance with FIG. 1.

In another embodiment, the present invention provides crystalline pirfenidone characterized by a differential scanning calorimetry (DSC) substantially in accordance with FIG. 2.

In another embodiment, the present invention provides a process for the purification of pirfenidone, comprising:
a) treating pirfenidone with alkaline base; and
b) isolating pure pirfenidone.

In another embodiment, the present invention provides a process for preparation of pirfenidone having less than 0.1% by HPLC of dimer impurity of Formula IV comprising: dissolving pirfenidone in an ester solvent or aromatic hydrocarbon solvent and isolating the pirfenidone.

In another embodiment, the present invention provides a process for preparing pirfenidone having a particle size with D90 from 50 microns to 500 microns, comprising:
a) dissolving pirfenidone in an organic solvent;
b) adding an anti-solvent to the above reaction mass; and
c) isolating the pirfenidone.

In another embodiment, the present invention provides a pharmaceutical composition comprising pirfenidone prepared by the process of the invention and at least one pharmaceutically acceptable excipient.

The present invention provides wet milling techniques for particle size reduction, which are suitable for sensitive materials that are having properties like dust explosive, shock sensitive and low ignition energy. Specifically, the present invention provides a process for reduction of particle size of pirfenidone by wet mill techniques. More specifically the present invention provides a process for particle size reduction of pirfenidone to below about 500 μm by wet mill techniques, which process avoids the aforementioned drawbacks associated with the known dry milling techniques.

In accordance with one embodiment, the present invention provides a process for particle size reduction of pirfenidone by wet milling.

In accordance with another embodiment, the present invention provides a process for particle size reduction of pirfenidone by wet milling in water.

In accordance with another embodiment, the present invention provides a process for particle size reduction of pirfenidone by wet milling using a suitable apparatus selected from colloid mill, ultrasonicator or high speed homogenizer.

In accordance with another embodiment, the present invention provides a process for particle size reduction of pirfenidone by wet milling using a suitable apparatus selected from colloid mill, ultrasonicator or high speed homogenizer in water.

In accordance with another embodiment, the present invention provides a process for particle size reduction of pirfenidone having a particle size distribution of above about 500 μm, by wet milling.

In accordance with another embodiment, the present invention provides a process for particle size reduction of pirfenidone having a particle size distribution of above about 500 μm, by wet milling using a suitable apparatus selected from colloid mill, ultrasonicator or high speed homogenizer.

In accordance with another embodiment, the present invention provides a process for particle size reduction of pirfenidone having a particle size distribution of above about 500 μm, by wet milling using a suitable apparatus selected from colloid mill, ultrasonicator or high speed homogenizer in water.

In accordance with another embodiment, the present invention provides a process for particle size reduction of pirfenidone having a particle size distribution of above about 500 μm, by wet milling; comprising: mixing pirfenidone having a particle size distribution of above about 500 μm in water for a sufficient period of time, and recovering the pirfenidone having a particle size distribution of below 500 μm.

In accordance with another embodiment, the present invention provides a process for particle size reduction of pirfenidone having a particle size distribution of above about 500 μm, by wet milling using a suitable apparatus; comprising: mixing pirfenidone having a particle size distribution of above about 500 μm in water for a sufficient period of time, and recovering the pirfenidone having a particle size distribution of below 500 μm; wherein the suitable apparatus is selected from colloid mill, ultrasonicator or high speed homogenizer.

In accordance with another embodiment, the present invention provides a process for particle size reduction of pirfenidone by wet milling using colloid mill.

In accordance with another embodiment, the present invention provides a process for particle size reduction of pirfenidone by wet milling using colloid mill in water.

In accordance with another embodiment, the present invention provides a process for particle size reduction of pirfenidone having a particle size distribution of above about 500 μm, by wet milling using colloid mill.

In accordance with another embodiment, the present invention provides a process for particle size reduction of pirfenidone having a particle size distribution of above about 500 μm, by wet milling using colloid mill in water.

In accordance with another embodiment, the present invention provides a process for particle size reduction of pirfenidone having a particle size distribution of above about 500 μm, by wet milling; comprising:
a) mixing pirfenidone having a particle size distribution of above about 500 μm with water,
b) circulating the step a) mixture in to colloidal mill, and
c) recovering the pirfenidone.

In accordance with another embodiment, the present invention provides a process for particle size reduction of pirfenidone having a particle size distribution of above about 500 μm, by wet milling using ultrasonicator.

In accordance with another embodiment, the present invention provides a process for particle size reduction of pirfenidone having a particle size distribution of above about 500 μm, by wet milling using ultrasonicator in water.

In accordance with another embodiment, the present invention provides a process for particle size reduction of pirfenidone having a particle size distribution of above about 500 μm, by wet milling; comprising:
a) mixing pirfenidone having a particle size distribution of above about 500 μm with water,
b) sonicating the step a) mixture in a ultrasonicator, and
c) recovering the pirfenidone.

In accordance with another embodiment, the present invention provides a process for particle size reduction of pirfenidone having a particle size distribution of above about 500 μm, by wet milling using high speed homogenizer.

In accordance with another embodiment, the present invention provides a process for particle size reduction of pirfenidone having a particle size distribution of above about 500 μm, by wet milling using high speed homogenizer in water.

In accordance with another embodiment, the present invention provides a process for particle size reduction of pirfenidone having a particle size distribution of above about 500 μm, by wet milling; comprising:

a) mixing pirfenidone having a particle size distribution of above about 500 μm with water in a high speed homogenizer, b) stirring the step a) mixture, and c) recovering the pirfenidone.

In accordance with another embodiment, the present invention provides a process for particle size reduction of pirfenidone having a particle size distribution of above about 500 μm, by wet milling using a suitable apparatus; comprising: mixing pirfenidone having a particle size distribution of above about 500 μm in water for a sufficient period of time, and recovering the pirfenidone having a particle size distribution of above about 10 μm and below about 500 μm; wherein the suitable apparatus is selected from colloid mill, ultrasonicator or high speed homogenizer.

In accordance with another embodiment, the present invention provides a process for particle size reduction of pirfenidone having a particle size distribution of above about 500 μm, by wet milling; comprising:

a) mixing pirfenidone having a particle size distribution of above 500 μm with water, b) circulating the step a) mixture in to colloidal mill, and c) recovering the pirfenidone having a particle size distribution of above about 10 μm and below about 500 μm.

In accordance with another embodiment, the present invention provides a pharmaceutical composition comprising pirfenidone prepared by the process of the invention and at least one pharmaceutically acceptable excipient.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE INVENTION

Figure 1:
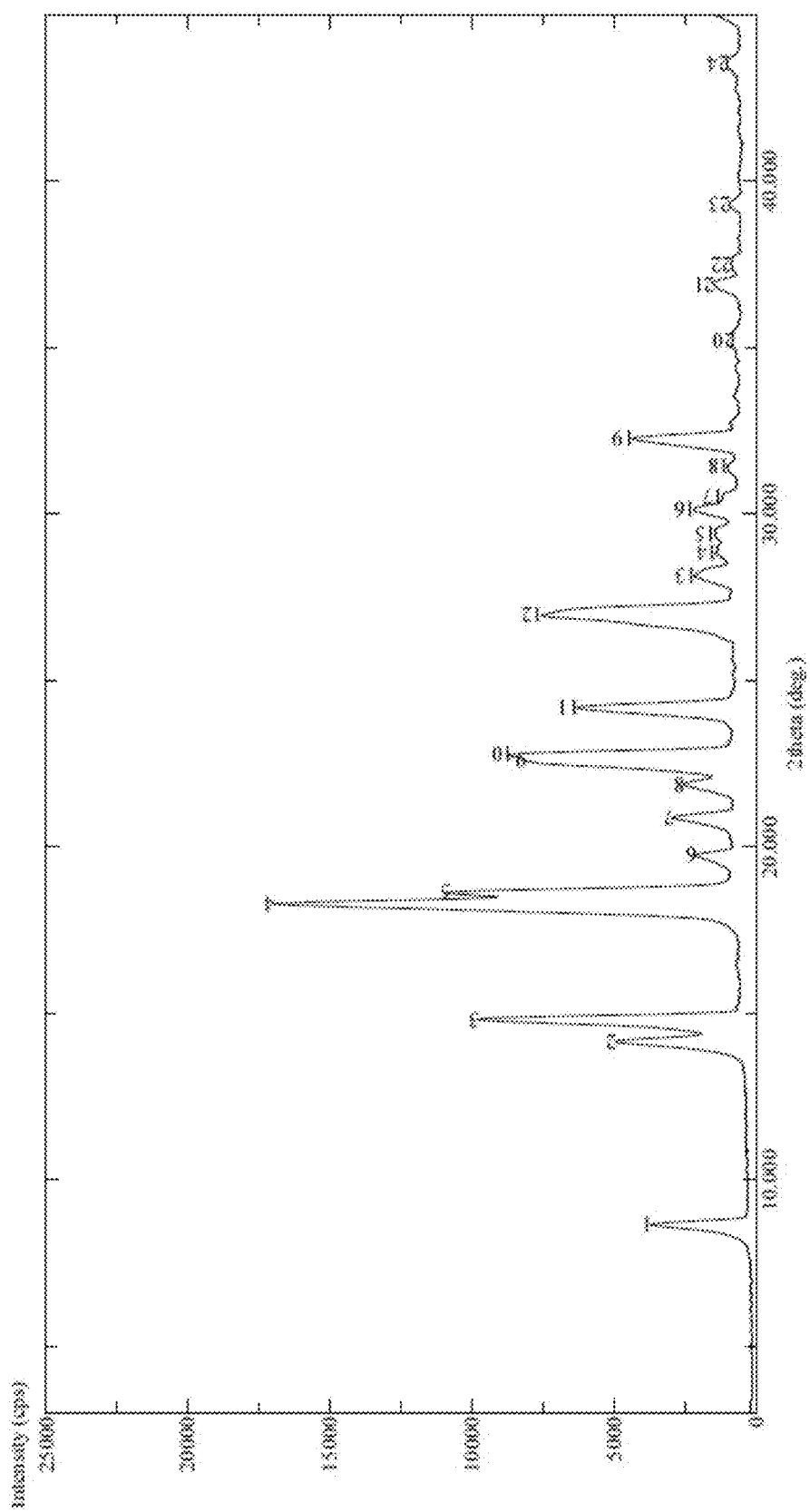
FIG. 1: illustrates the characteristic powder X-ray diffraction (XRD) pattern of crystalline pirfenidone.

The present invention provides an improved process for the preparation of pure pirfenidone using the commercially available bromobenzene having about 0.2% or more by weight dibromobenzene.

According to U.S. patent publication U.S. Pat. No. 8,519, 140, the purity of the bromobenzene is more important for the preparation of pirfenidone, as amount of dibromobenzene impurity in the bromobenzene leads to produce dimer-type byproducts, which are difficult to remove from final pirfenidone using regular purification techniques. In order to control the dimer impurity, the '140 patent utilizes bromobenzene having less than 0.15% by weight dibromobenzene. The present invention provides an improved process for preparation of pure pirfenidone utilizing commercially available bromobenzene having about 0.2% or more by weight dibromobenzene. Thereby avoiding the sourcing difficulties and cost associated with sourcing of bromobenzene with particular purity level.

In one embodiment, the present invention provides an improved process for the preparation of pirfenidone of formula (I)

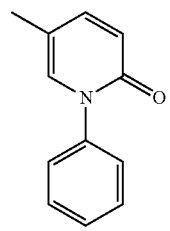

Formula (I)

which comprise the reaction of 5-methyl-1H-pyridin-2-one of formula (II)

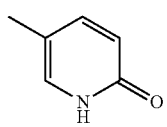

Formula (II)

with bromobenzene of formula (III)

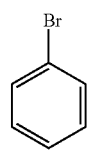

Formula (III)

in the presence of a suitable copper catalyst and a base in a suitable organic solvent under sufficient conditions to provide pirfenidone, wherein the bromobenzene contain about 0.2% or more by weight dibromobenzene.

The starting material 5-methyl-1H-pyridin-2-one of formula (II) can be prepared by the methods known in the art or by the method exemplified herein the present invention.

The another starting material bromobenzene of formula (III) is commercially available and having dibromobenzene isomer content such as 1,4-dibromobenzene, 1,3-dibromobenzene and 1,2-dibromobenzene, is in the range of about 0.2% to about 1% w/w.

The suitable copper catalyst used herein for the reaction of formula (II) with formula (III) is selected from copper (I) chloride, copper (I) bromide, copper(I) iodide and the like. Preferably copper (I) chloride.

The suitable base used herein is selected from alkali metal carbonates such as potassium carbonate, potassium bicarbonate, sodium carbonate, sodium bicarbonate and the like; alkali metal hydroxide such as potassium hydroxide, sodium hydroxide, lithium hydroxide and the like, or mixtures thereof organic base such as triethylamine, diisopropylethylamine and the like. Preferably the suitable base is potassium carbonate.

The suitable organic solvent used herein is selected from hydrocarbon solvents such as benzene, chlorobenzene, toluene, xylene, heptane, hexane, cyclohexane, methyl cyclohexane, cyclopentane and the like; amide solvents such as dimethylacetamide, dimethylformamide, N-methylformamdide, dimethylimidazolidinone, N-methyl pyrrolidinone and the like; dimethylsulfoxide; and mixtures thereof. Preferably, the suitable solvent is dimethylformamide.

The reaction of formula (II) with formula (III) can be suitably carried out at a temperature of about 30° C. to about 180° C., preferably at about 100° C. to about 160° C. for sufficient period of time to complete the reaction, preferably for 1 to 24 hrs, more preferably for 8-12 hrs. The product formed can be isolated by the techniques known in the art; preferably by filtration.

In another embodiment, the present invention provides a process for the purification of pirfenidone, comprising:

a) treating pirfenidone with alkaline base; and b) isolating pure pirfenidone.

The starting pirfenidone and alkaline base is taken in a flask at about 25° C. to about 35° C. and raising the reaction mass temperature at about 70 to about 90° C. to completely dissolving the reactants. Then, isolating the pure pirfenidone by methods known in the art, for example, cooling the reaction mass to below about 20° C. followed by filtration and drying at suitable temperature. The suitable alkaline base is selected from sodium hydroxide, potassium hydroxide, sodium carbonate, potassium carbonate, sodium bicarbonate, potassium bicarbonate and the like, and mixtures thereof; preferably aqueous sodium hydroxide solution.

In another embodiment the present invention provides crystalline pirfenidone characterized by its Powder X-ray diffractogram having one or more peaks at about 8.76, 14.22, 14.90, 18.36, 18.72, 19.86, 20.90, 21.92, 22.52, 22.86, 24.22, 26.96, 27.20, 28.16, 28.80, 29.50, 30.20, 31.42, 32.32, 37.02, 39.40 and 43.38±0.2°2θ or by a powder X-Ray diffraction (PXRD) pattern substantially in accordance with FIG. 1.

The diffractogram of FIG. 1 was measured on a Regaku Mini Flex-II Powder X-ray powder Diffractometer equipped with a Cu-anode ([A]=1.54 A), having an X-ray source operated at 30 kV, 15 mA and a Ni filter used to strip K-beta radiation. Measuring range: 3-45° 2θ; step width: 0.020°; and scan speed=5°/minute.

Figure 2:
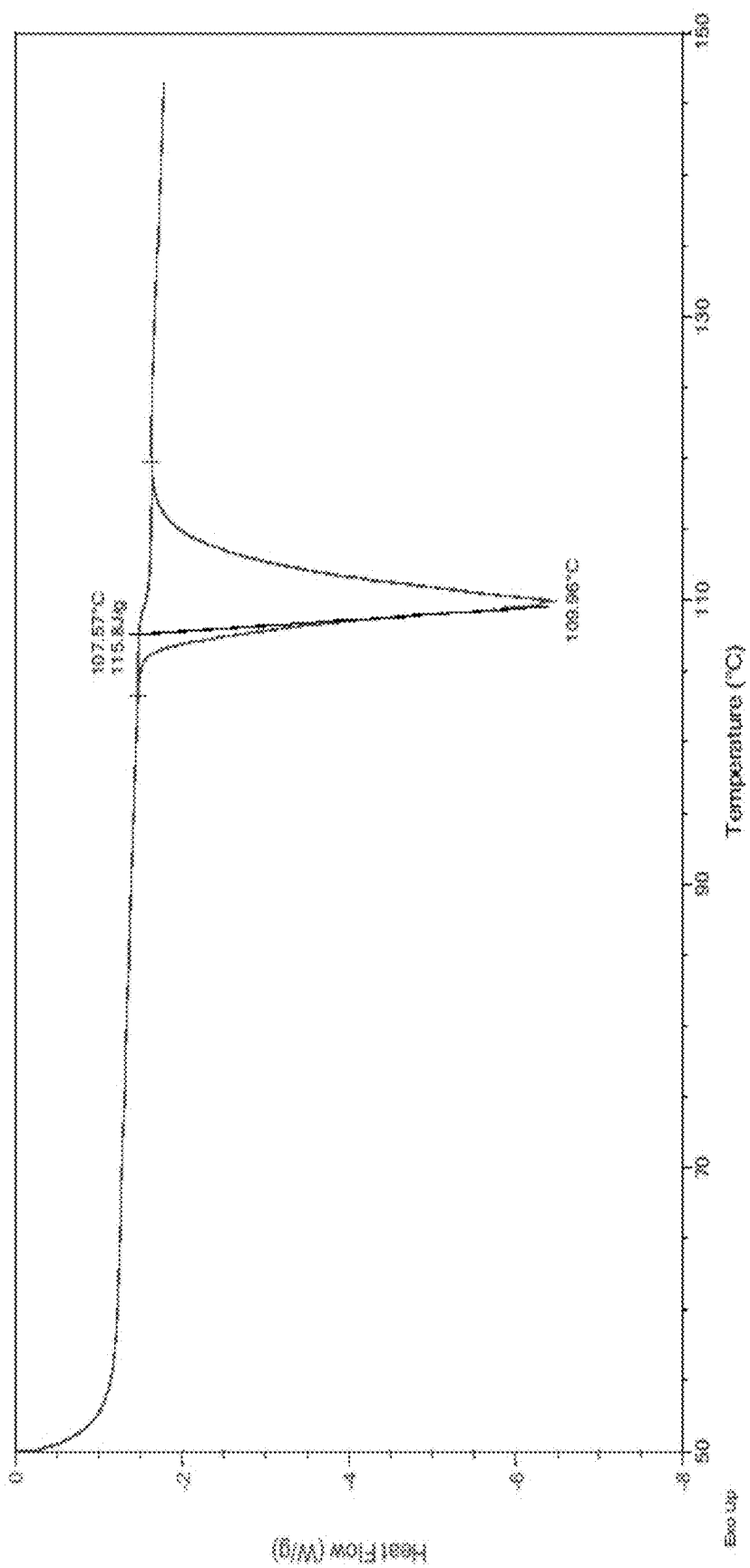
FIG. 2: illustrates the characteristic differential scanning calorimetric (DSC) thermogram of crystalline pirfenidone.

In another embodiment, the present invention provides crystalline pirfenidone characterized by a differential scanning calorimetry (DSC) substantially in accordance with FIG. 2.

The DSC data of FIG. 2 was measured on a DSC Q200, TA instrumentation, Waters, using a hermitically sealed aluminium pan over a temperature range of 50° C.-150° C. with a ramp rate of 10° C./min.

In another embodiment, the present invention provides a process for preparation of pirfenidone having less than 0.1% by HPLC of dimer impurity of Formula IV, comprising: dissolving pirfenidone in an ester solvent or aromatic hydrocarbon solvent and isolating the pirfenidone.

The dimer impurity of pirfenidone represented by the following structural formula (IV)

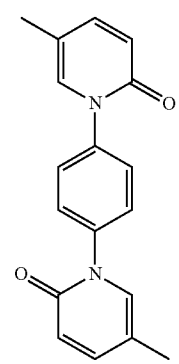

Formula (IV)

The process of dissolving pirfenidone in an ester solvent or aromatic hydrocarbon solvent is carried out at a temperature of about 25° C. to about reflux, preferably at reflux temperature. The esters include, but are not limited to ethyl acetate, methyl acetate, isopropyl acetate and the like; aromatic hydrocarbons such as toluene, xylene and the like; preferably ethyl acetate or toluene. In order to form a solution, the contents may be stirred for sufficient period of time, preferably for about 10 min to about 30 min for complete dissolution. Then, the solution may be optionally concentrated to partially reduce the solvent volume and cooled to a temperature from about 25° C. or less such that the pirfenidone can be isolated by conventional techniques, for example by filtration.

In another embodiment, the present invention provides a process for preparing pirfenidone having a particle size with D90 from 50 microns to 500 microns, comprising:

a) dissolving pirfenidone in an organic solvent;

b) adding an anti-solvent to the above reaction mass; and c) isolating the pirfenidone.

Step a) of the forgoing process involves the dissolution of pirfenidone in an organic solvent, wherein the organic solvent includes but are not limited to aromatic hydrocarbons such as toluene, xylene and the like; esters such as isopropyl acetate, methyl acetate, ethyl acetate, n-propyl acetate, n-butyl acetate, t-butyl acetate and the like; alcohols such as methanol, ethanol, isopropanol, n-propanol, n-butanol, isobutanol and the like; ketones such as acetone, methyl ethyl ketone, methyl isobutyl ketone and the like; ethers such as methyl tertiary butyl ether, tetrahydrofuran, dimethyl ether, diisopropyl ether, 1,4-dioxane or mixtures thereof.

Optionally the reaction mixture may be heated to complete dissolution of the contents in the solvent. The suitable temperature may be selected from 35° C. to about reflux temperature of the solvent used; preferably at about 50° C. to about 65° C.

Adding the solution obtained in step a) to the anti-solvent, or adding an anti-solvent to the solution obtained in step iv) to effect the crystallization of the product; preferably the antisolvent is added to step a) reaction solution.

The anti-solvent used for step b) includes but are not limited to water, hydrocarbon solvents such as n-pentane, n-hexane, n-heptane, cyclohexane, methyl cyclohexane, cycloheptane or mixture thereof.

The addition of antisolvent at different temperatures leads to formation of pirfenidone particles with different sizes; for instance: anti solvent addition at 0 to −10° C., preferably at −5±2° C. temperature forms small particles (D90: 50-100µ), at 0 to 10° C., preferably at 7±3° C. temperature forms particles of D90 at 100-150µ and at below 45° C. forms particles of D90 at 250-500µ.

In step c) of the foregoing process involves the isolation of pirfenidone. The isolation can be carried out by conventional techniques known in the art, for example filtration.

The step c) of the isolation of the pirfenidone is particularly carried out by stirring the step b) reaction solution at less than about 30° C., preferably at about 0-5° C., at about 5-10° C. and at about room temperature for about 10 minutes to about 4 hours and the precipitated crystals can be isolated by methods known in the art, filtration, followed by drying the resultant crystals at temperature below 65° C. under vacuum.

The pirfenidone prepared according to the present invention is having purity of at least about 98% as measured by HPLC, preferably at least about 99% as measured by HPLC; more preferably at least about 99.5% as measured by HPLC.

In another embodiment, the present invention provides a pharmaceutical composition comprising pirfenidone prepared by the process of the invention and at least one pharmaceutically acceptable excipient.

EXAMPLES

The following examples are provided by way of illustration only, and are not intended to be limiting of the present invention. Further, the present invention covers all the possible combinations of particular and preferred embodiments indicated herein.

Example 1

Preparation of 5-methyl-1H-pyridin-2-one

DM water (800 ml) was added to concentrated sulfuric acid (227 g) at 0-5° C. and stirred for 15 mins. To this, 2-amino-5-methyl pyridine (100 g) followed by aqueous sodium nitrite (83 g of sodium nitrite dissolved in 200 ml of water) was added at below 10° C. The reaction mass was stirred for an hour at 0-5° C. After the reaction completion, reaction mass temperature was raised to 25-35° C. and stirred for 4 hrs. Aqueous sulphamic acid (26.9 g of sulphamic acid dissolved in 100 ml of water) was added to the reaction mass and stirred for 60 mins at 25-35° C. The reaction mass was cooled to 10-15° C. and pH was adjusted to 7 with aqueous sodium hydroxide solution. The reaction mass was heated to 55-65° C. and extracted with ethyl acetate (6×500 ml). The solvent from the extract was distilled off completely under mild vacuum at below 60° C. Ethyl acetate (200 ml) was added to the obtained residue and the reaction mixture was cooled to 25-35° C. then stirred for an hour. The precipitated solid was filtered, washed with ethyl acetate and dried at 45-55° C.

Yield: 80 g

Example 2

Preparation of Pirfenidone

A mixture of 5-methyl-1H-pyridin-2-one (100 g), bromobenzene (259 g, comprising greater than 0.2% by weight dibromobenzene isomers) and dimethylformamide (200 ml) were added in to a round bottom flask and stirred up to complete dissolution. Potassium carbonate (254 g) and copper (I) chloride (18.2 g) was added to the above reaction mass and then heated to 130-140° C. The reaction mass was stirred at 130-140° C. for 10 hrs. After the reaction completion, the reaction mass was cooled to 25-35° C. Toluene (500 ml), aqueous sodium chloride (75 g of sodium chloride in 500 ml of water) was added to the reaction mass and stirred for 15-30 mins at 25-35° C. The reaction mass was filtered and the filtrate was allowed to settle. Organic and aqueous layers were separated and the aqueous layer was extracted with toluene. Organic layers combined and was washed with aqueous sodium chloride, treated with carbon and filtered through hyflo. The solvent from the filtrate was distilled off completely under vacuum at below 60° C. Toluene (300 ml) was added to the obtained residue and stirred for 30 mins. The reaction mass was heated to 77-83° C. and stirred for 45 mins. The reaction mass was cooled to 25-35° C. over 60 mins. The reaction mass was further cooled to 0-6° C. The solid obtained was filtered, washed with toluene and dried under vacuum. DM water (500 ml) was added to the above obtained wet compound followed by 50% aqueous sodium hydroxide solution (10 g of sodium hydroxide in 20 ml of water) at 25-35° C. The reaction mass was heated to 75-85° C. and stirred for 30-60 mins. The reaction mass was then gradually cooled to 25-35° C. and stirred for 60 mins. The reaction mass was further cooled to 0-5° C. and stirred for 3 hrs. The obtained solid was filtered, washed with water and dried to provide the title compound.

Yield: 120 g;
Purity by HPLC: 99%;
The XRPD is set forth in FIG. 1;
The DSC is set forth in FIG. 2.

Example 3

Purification of Pirfenidone (from Ethyl Acetate)

A suspension of crude Pirfenidone (50 g), contaminated with the dimer impurity (~0.14% by HPLC) in ethyl acetate (100 mL) was maintained at 65-75° C. till the material completely dissolved. The reaction mass was treated with activated carbon (5 g) and filtered through a short bed of Hyflo. The flask was rinsed with hot ethyl acetate (50 mL) and the combined filtrate was partially concentrated, under reduced pressure (till ~2.0 volumes remaining in the flask), while maintain temperature below 60° C. The mixture was gradually cooled to 30±5° C. and then stirred for another 30-60 min. The suspension was cooled to 0-5° C. and maintained for another 2-3 h, at the same temperature. The precipitated material was filtered and then dried at 60±5° C., for 6-8 h, to afford Pirfenidone as white colored powder. Yield: 45 g, HPLC purity 99.9%; dimer content 0.03%.

Example 4

Purification of Pirfenidone (from Toluene)

A suspension of crude Pirfenidone (59 g), contaminated with the dimer impurity (~0.14% by HPLC) in toluene (150 mL) was maintained at 75-85° C. till the material completely dissolved. The reaction mass was treated with activated carbon (5 g) and filtered through a short bed of Hyflo. The flask was rinsed with hot toluene (50 mL) and the combined filtrate was again heated to 75-85° C. and then gradually cooled to 30±5° C. and then stirred for another 30-60 min. The suspension was cooled to 0-5° C. and maintained for another 2-3 h, at the same temperature. The precipitated material was filtered and then dried at 60±5° C., for 6-8 h, to afford Pirfenidone as white colored powder. Yield: 41 g, HPLC purity 99.9%; dimer content 0.07%.

Purification of Pirfenidone (from ethyl acetate+n-heptane):

Example 5

Pirfenidone (83 g) was dissolved in ethyl acetate (425 mL), at 55-65° C., and then added to pre-cooled (−5±2° C.) n-Heptane (425 mL), over a period of 15-20 min, while maintaining temperature below 20° C. The suspension was stirred, at 0-5° C., for 1-2 h; filtered the product washed with chilled ethyl acetate (50 mL). The wet material was dried, at 60° C., under vacuum, for 6-8 h, to afford Pirfenidone as white colored powder. Yield: 65 g, HPLC purity 99.9%, PSD: ($D_{90}$) 50-100μ.

Example 6

Pirfenidone (81 g) was dissolved in ethyl acetate (425 mL), at 55-65° C., and then added to pre-cooled (7±3° C.) n-Heptane (425 mL), over a period of 15-20 min, while maintaining temperature below 20° C. The suspension was stirred, at 0-5° C., for 1-2 h; filtered the product washed with chilled ethyl acetate (50 mL). The wet material was dried, at 60° C., under vacuum, for 6-8 h, to afford Pirfenidone as white colored powder Yield: 61 g, HPLC purity 99.9%, PSD: ($D_{90}$) 100-150μ.

Example 7

Pirfenidone (81 g) was dissolved in ethyl acetate (500 mL), at 50-55° C., and then added to pre-cooled (8±3° C.) n-Heptane (500 mL), over a period of 15-20 min, while maintaining temperature below 25° C. The suspension was stirred, at 5-10° C., for 1-2 h; filtered the product washed with chilled ethyl acetate (50 mL). The wet material was dried, at 60° C., under vacuum, for 6-8 h, to afford Pirfenidone as white colored powder Yield: 57 g, HPLC purity 99.9%, PSD: ($D_{90}$) 150-250μ.

Example 8

Pirfenidone (80 g) was dissolved in ethyl acetate (400 mL), at 55-65° C., and then added to n-Heptane (400 mL), over a period of 5-10 min, while maintaining temperature below 45° C. The suspension was stirred, at 25-30° C., for 1-2 h; filtered the product washed with chilled ethyl acetate (50 mL). The wet material was dried, at 60° C., under vacuum, for 6-8 h, to afford Pirfenidone as white colored powder, Yield: 55 g, HPLC purity 99.9%, PSD: ($D_{90}$) 250-500μ.

The present invention provides wet milling techniques for particle size reduction, which are suitable for sensitive materials that are having properties like dust explosive, shock sensitive and low ignition energy. Specifically, the present invention provides a process for particle size reduction of pirfenidone by wet mill techniques. More specifically the present invention provides a process for particle size reduction of pirfenidone to below about 500 μm by wet mill techniques, which process avoids the aforementioned drawbacks associated with the known dry milling techniques.

The known milling processes involve dry milling of pirfenidone by loop mill method. The loop mill grinds materials by using a high speed jet of compressed air or inert gas in dry state to impact particles into each other. Dry milling process used in the loop mill particle size reduction always generates an energetic particle that generates thermal energy which generally leads to explosion or burnings. The present milling process involves milling of pirfenidone in wet medium preferably in aqueous medium, wherein the thermal energy generated by the energetic particles is absorbed by the moisture on the particle surfaces and thereby preventing explosion or burning caused by localized hot spots. Thus, the process is safer than the dry milling processes, particularly in the commercial scale operations.

As used herein, the term "particle size distribution" is expressed in terms of $D_{90}$, $D_{50}$ and $D_{10}$, which corresponds to the diameter of 90 percent by volume of the particles, 50 percent by volume of the particles and 10 percent by volume of the particles are present, respectively.

As used herein, the term "recovering" refers to a process of obtaining pirfenidone by means of filtration, decantation, extraction, distillation, evaporation, centrifugation or a combination thereof.

As used herein, the term "mixing" refers to suspending pirfenidone in a medium.

As used herein, the term "about" refers to a variation of 10% from the indicated values, or in case of a range of values, means a 10% variation from both the lower and upper limits of such ranges.

As used herein, the starting material pirfenidone having a particle size distribution of above about 500 μm may be obtained from any processes known in the art; preferably the starting material used herein is obtained from reference examples 4 & 5.

In accordance with one embodiment, the present invention provides a process for particle size reduction of pirfenidone by wet milling.

In another embodiment, the present invention provides a process for particle size reduction of pirfenidone by wet milling using a suitable apparatus selected from colloid mill, ultrasonicator or high speed homogenizer.

In another embodiment, the present invention provides a process for particle size reduction of pirfenidone by wet milling in water using a suitable apparatus selected from colloid mill, ultrasonicator or high speed homogenizer.

In another embodiment, the present invention provides a process for particle size reduction of pirfenidone having a particle size distribution of above about 500 μm, by wet milling using a suitable apparatus selected from colloid mill, ultrasonicator or high speed homogenizer.

Colloid Mill:

In a specific embodiment, the present invention provides a process for particle size reduction of pirfenidone by wet milling using colloid mill.

In accordance with another embodiment, the present invention provides a process for particle size reduction of pirfenidone by wet milling using colloid mill in water.

In accordance with another embodiment, the present invention provides a process for particle size reduction of pirfenidone having a particle size distribution of above about 500 μm, by wet milling using colloid mill.

In accordance with another embodiment, the present invention provides a process for particle size reduction of pirfenidone having a particle size distribution of above about 500 μm, by wet milling; comprising:

a) mixing pirfenidone having a particle size distribution of above about 500 μm with water,
b) circulating the step a) mixture in to colloidal mill, and
c) recovering the pirfenidone.

Colloid mill is a machine used in the process of milling of solid particles to reduce size of the particles or making homonization of the solid particles present in suspension or emulsion. Colloid mill instrument and method of milling for the use of pharmaceutical products is known from the art; for example Colloid mill instrument used in the present invention is having following identification: Colloid mill/IKA MK 2000/05 or any equivalent colloid mill instrument can be used as long as pirfenidone with required particle size is produced during the process of the invention.

The input pirfenidone may be any crystalline or other form of pirfenidone with any particle size preferably above about 500 µm, including various solvates, hydrates, salts and co-crystals as long as pirfenidone with required particle size is produced during the process of the invention or pirfenidone obtaining as existing slurry from a previous processing step.

The aforementioned step a) process involves mixing pirfenidone having a particle size distribution of above about 500 µm with water. Then the resultant step a) mixture is circulated in to colloid mill. The circulation temperature should be sufficient to form the required particle size. Typically the circulation temperature can be from about 5° C. to about 65° C.; preferably at about 25° C. to about 50° C.

Reduction of particle size of the invention is dependent on the number of revolutions per minute (rpm) of the colloid mill and duration of circulation of the reaction suspension. The rpm and the circulation time are not particularly limited to specific values but an exemplary the same may be employed in the range of about 500 to about 10000 rpm for a period of about 5 minutes to about 30 hours; preferably about 1000 to about 8000 rpm for a period of about 30 minutes to about 24 hours.

After attaining the required particle size, preferably to below 500 µm, the resultant product may be recovered by known methods, for example decantation, filtration and the like; preferably by filtration. Optionally before recovery of the product, the reaction mixture may be allowed to cool to about 0° C. to about 15° C. and stirred for about 30 min to 10 hours at same temperature. The resultant product may be dried using conventional methods known in the art at a temperature ranging from about 40° C. to about 75° C. for a period of 2 hours to 10 hours. Preferably drying is carried out at about 50° C. to about 65° C. for a period of 4 hours to 6 hours.

Pirfenidone particles obtained by the reduction process using colloid mill is having a particle distribution of about $D_{10}$ less than 50 µm, preferably less 20 µm; $D_{50}$ less than 100 µm, preferably 50 µm; D90 less than 200 µm, preferably 100 µm.

Ultrasonication:

In another embodiment, the present invention provides a process for particle size reduction of pirfenidone having a particle size distribution of above about 500 µm, by wet milling using ultrasonicator.

In another embodiment, the present invention provides a process for particle size reduction of pirfenidone having a particle size distribution of above about 500 µm, by wet milling using ultrasonicator in water.

In a preferred embodiment, the present invention provides a process for particle size reduction of pirfenidone having a particle size distribution of above about 500 µm, by wet milling; comprising:

a) mixing pirfenidone having a particle size distribution of above about 500 µm with water, b) sonicating the step a) mixture in a ultrasonicator, and c) recovering the pirfenidone.

Ultrasonication is an efficient means for the wet-milling and micro-grinding of particles. In particular for the manufacturing of superfine-size slurries, ultrasonication has many advantages, when compared with common size reduction equipment, such as: ball mills, bead mills, disc mills or jet mills. Ultrasonication allows for the processing of high-concentration and high-viscosity slurries—therefore reducing the volume to be processed. Ultra sonic waves do not allow agglomerates to form as observed during conventional crystallization process. Accordingly, sonication is a safe process that allows easy scale up based on constant power per unit volume.

The input pirfenidone may be any crystalline or other form of pirfenidone with any particle size preferably above about 500 µm, including various solvates, hydrates, salts and cocrystals as long as pirfenidone with required particle size is produced during the process of the invention or pirfenidone obtaining as existing slurry from a previous processing step.

The step of mixing pirfenidone having a particle size distribution of above about 500 µm with water is placed in an ultrasonicator and sonicating for a sufficient period of time. The ultrasonicator temperature should be sufficient to form the required particle size. Typically the sonication temperature can be from about 5° C. to about 65° C. for a period of about 30 min to about 10 hours. Preferably the sonication temperature is about 25° C. to about 50° C. for a period of about 1 hour to about 5 hours.

After attaining the required particle size, preferably to below 500 µm, the resultant product may be recovered by known methods, for example decantation, filtration and the like; preferably by filtration. Optionally before recovery of the product, the reaction mixture may be allowed to cool to about 0° C. to about 15° C. and stirred for about 30 min to 10 hours at same temperature. The resultant product may be dried using conventional methods known in the art at a temperature ranging from about 40° C. to about 75° C. for a period of 2 hours to 10 hours. Preferably drying is carried out at about 50° C. to about 65° C. for a period of 4 hours to 6 hours.

Pirfenidone particles obtained by the reduction process after ultrasonication is having a particle distribution of about $D_{10}$ less than 50 µm, preferably less 30 µm; $D_{50}$ less than 150 preferably 100 µm; D90 less than 300 µm, preferably 250 µm.

High Speed Homogenizer:

In another embodiment, the present invention provides a process for particle size reduction of pirfenidone having a particle size distribution of above about 500 µm, by wet milling using high speed homogenizer.

In another embodiment, the present invention provides a process for particle size reduction of pirfenidone having a particle size distribution of above about 500 µm, by wet milling using high speed homogenizer in water.

In a preferred embodiment, the present invention provides a process for particle size reduction of pirfenidone having a particle size distribution of above about 500 µm, by wet milling; comprising:

a) mixing pirfenidone having a particle size distribution of above about 500 µm with water in a high speed homogenizer, b) stirring the step a) mixture, and c) recovering the pirfenidone.

The input pirfenidone may be any crystalline or other form of pirfenidone with any particle size preferably above about 500 µm, including various solvates, hydrates, salts and cocrystals as long as pirfenidone with required particle size is produced during the process of the invention or pirfenidone obtaining as existing slurry from a previous processing step.

The step of mixing pirfenidone having a particle size distribution of above about 500 μm with water is placed in high speed homogenizer and stir for a sufficient period of time. The high speed homogenizer temperature should be sufficient to form the required particle size. Typically the stirring temperature can be from about 5° C. to about 65° C. for a period of about 30 min to about 10 hours. Preferably the stirring temperature is about 25° C. to about 50° C. for a period of about 1 hour to about 5 hours.

The stirring speed of the reaction mixture is not particularly limited but may be employed in the range of 500-10000 rounds per minute, preferably 1000-7000 rounds per minute.

After attaining the required particle size, preferably to below 500 μm, the resultant product may be recovered by known methods, for example decantation, filtration and the like; preferably by filtration. Optionally before recovery of the product, the reaction mixture may be allowed to cool to about 0° C. to about 15° C. and stirred for about 30 min to 10 hours at same temperature. The resultant product may be dried using conventional methods known in the art at a temperature ranging from about 40° C. to about 75° C. for a period of 2 hours to 10 hours. Preferably drying is carried out at about 50° C. to about 65° C. for a period of 4 hours to 6 hours.

The resultant product may be further dried using conventional methods known in the art at a temperature ranging from about 40° C. to about 75° C. for a period of 2 hours to 10 hours. Preferably drying is carried out at about 50° C. to about 65° C. for a period of 4 hours to 6 hours.

Pirfenidone particles obtained by the reduction process after high speed homogenizer is having a particle distribution of about $D_{10}$ less than 50 μm, preferably less 30 μm; $D_{50}$ less than 150 μm, preferably 100 μm; D90 less than 300 μm, preferably 250 μm.

In another embodiment, the present invention provides a pharmaceutical composition, comprising pirfenidone prepared by the processes of the present invention and at least one pharmaceutically acceptable excipient. Such pharmaceutical composition may be administered to a mammalian patient in any dosage form, e.g., solid, liquid, powder, injectable solution, etc.

The particle size distribution of pirfenidone is measured utilizing: Instrument model: Malvern; Mastersizer 3000; particle refraction index of sample: 1.700; Absorption: 0.01 and Analysis model: general purpose, normal sensitivity, non-spherical particles.

Additional Examples

The following non limiting examples illustrate specific embodiments of the present invention. They are not intended to be limiting the scope of the present invention in any way.

Example 9

Particle size reduction of pirfenidone using colloid mill (IKA MK 2000/05)

Pirfenidone (Particle size distribution: $D_{10}$: 1330 μm; $D_{50}$: 1950 μm and $D_{90}$: 2840 μm) and Water (3 vol) were charged into IKA colloid mill at 25° C. to 35° C. and circulated the reaction mass at 25° C. to 35° C. till required particle size was obtained. Particle size distribution of the sample with different time interval was monitored by collecting the sample from reaction mass. After achieving the required particle size, stirred the reaction mixture for 30-60 min at 25° C. to 35° C. Further, the reaction mixture temperature was allowed to cool to 0° C. to 5° C. and stirred for 2-3 hrs at same temperature. Filter the solid and washed with the wet cake with chilled water (0.5 vol), dried the solid in an oven under vacuum at 60° C. for 4-6 hours.

The following examples were performed using the above described process with different circulation time and different rpm and obtained results are tabulated as below:

TABLE 1

| Ex. No. | Input | Out put | rpm | Circulation time | PSD $D_{10}$ | PSD $D_{50}$ | PSD $D_{90}$ |
|---|---|---|---|---|---|---|---|
| 1A | 20 kg | 17 kg | 6000 | 1 hour | 30 μm | 105 μm | 206 μm |
| | | | | 2 hours | 28 μm | 72 μm | 165 μm |
| | | | | 3 hours | 26 μm | 61 μm | 143 μm |
| | | | | 4 hours | 23 μm | 54 μm | 129 μm |
| | | | | 5 hours | 22 μm | 53 μm | 117 μm |
| | | | | 6 hours | 21 μm | 49 μm | 107 μm |
| 1B | 200 kg | 180 kg | 6000 | 45 min | 41 μm | 48 μm | 285 μm |
| | | | | 2 hours | 34 μm | 124 μm | 257 μm |
| | | | | 3 hours | 34 μm | 116 μm | 236 μm |
| | | | | 4 hours | 32 μm | 106 μm | 222 μm |
| | | | | 5 hours | 33 μm | 106 μm | 217 μm |
| | | | | 6 hours | 29 μm | 101 μm | 200 μm |
| | | | | 7 hours | 31 μm | 94 μm | 200 μm |
| | | | | 8 hours | 28 μm | 84 μm | 187 μm |
| | | | | 9 hours | 28 μm | 80 μm | 180 μm |
| | | | | 10 hours | 27 μm | 69 μm | 155 μm |
| | | | | 12 hours | 25 μm | 61 μm | 150 μm |
| 1C | 80 kg | 71 kg | 6000 | 8 hours | 21 μm | 57 μm | 132 μm |
| | | | | 10 hours | 22 μm | 55 μm | 122 μm |
| | | | | 12 hours | 22 μm | 54 μm | 121 μm |
| | | | | 14 hours | 21 μm | 47 μm | 98 μm |
| | | | | 16 hours | 21 μm | 47 μm | 96 μm |
| | | | | 19 hours | 22 μm | 46 μm | 93 μm |
| 1D | 200 gr | 180 gr | 3000 | 30 min | 28 μm | 87 μm | 185 μm |
| 1E | 200 gr | 175 gr | 3000 | 60 mim | 12 μm | 33 μm | 123 μm |
| 1F | 200 gr | 170 gr | 3000 | 120 mim | 13 μm | 33 μm | 82 μm |
| 1G | 200 gr | 185 gr | 5000 | 5 min | 11 μm | 40 μm | 99 μm |

TABLE 1-continued

| Ex. No. | Input | Output | rpm | Circulation time | PSD $D_{10}$ | PSD $D_{50}$ | PSD $D_{90}$ |
|---|---|---|---|---|---|---|---|
| 1H | 200 gr | 175 gr | 5000 | 60 min | 11 μm | 36 μm | 89 μm |
| 1I | 200 gr | 175 gr | 8000 | 5 min | 9 μm | 35 μm | 85 μm |

Example 10

Particle size reduction of pirfenidone using high speed homogenizer (Silverson L5M-A Lab Mixer)

Water (300 mL) and Pirfenidone (100 gr; Particle size distribution: $D_{10}$: 1330 μm; $D_{50}$: 1950 μm and $D_{90}$: 2840 μm) were charged into reaction vessel at 25° C. to 35° C. and was placed High speed stirrer/Homogenizer into the reaction mass till required particle size was obtained at 25° C. to 35° C. Particle size distribution of the sample with different time interval was monitored by collecting the sample from reaction mass. After achieving the required particle size, stirred the reaction mixture for 30-60 min at 25° C. to 35° C. Further, the reaction mixture temperature was allowed to cool to 0° C. to 5° C. and stirred for 2-3 hrs at same temperature. Filter the solid and washed with the wet cake with chilled water (100 mL), dried the solid in an oven under vacuum at 60° C. for 4-6 hours.

The following examples were performed using the above described process with different rpm and time; the obtained results are tabulated below:

TABLE 2

| Exp. No | Input Wt. | Output Wt. | RPM | Stirring time | PSD $D_{10}$ | PSD $D_{50}$ | PSD $D_{90}$ |
|---|---|---|---|---|---|---|---|
| 2A | 100 g | 90 g | 2000 | 30 min | 24 μm | 82 μm | 230 μm |
| 2B | 100 g | 87 g |  | 60 min | 24 μm | 88 μm | 200 μm |
| 2C | 100 g | 84 g |  | 120 min | 21 μm | 75 μm | 165 μm |
| 2D | 100 g | 80 g |  | 240 min | 21 μm | 71 μm | 154 μm |
| 2E | 100 g | 85 g | 5000 | 60 min | 17 μm | 48 μm | 108 μm |
| 2F | 100 g | 86 g | 7000 | 60 min | 13 μm | 42 μm | 91 μm |

Example 11

Particle size reduction of pirfenidone using ultra sonication by sonoprocessor (RTUL 10SP-20-3000-SD)

Water (300 mL) and Pirfenidone (200 gr; Particle size distribution: $D_{10}$: 1330 μm; $D_{50}$: 1950 μm and $D_{90}$: 2840 μm) were charged into reaction vessel at 25° C. to 35° C. and was placed Sonoprocessor into the reaction mass till required particle size was obtained at 25° C. to 35° C. Particle size distribution of the sample with different time interval was monitored by collecting the sample from reaction mass. After achieving the required particle size, stirred the reaction mixture for 30-60 min at 25° C. to 35° C. Further, the reaction mixture temperature was allowed to cool to 0° C. to 5° C. and stirred for 2-3 hrs at same temperature. Filter the solid and washed the wet cake with chilled water (100 mL), dried the solid in an oven under vacuum at 60° C. for 4-6 hours.

The following examples were performed using the above described process with different rpm and time; the obtained results are tabulated below:

TABLE 3

| Exp. No | Input Wt. | Output Wt. | Sonication time | PSD $D_{10}$ | PSD $D_{50}$ | PSD $D_{90}$ |
|---|---|---|---|---|---|---|
| 3A | 200 g | 183 g | 30 min | 44 μm | 145 μm | 245 μm |
| 3B | 200 g | 180 g | 60 min | 26 μm | 101 μm | 189 μm |
| 3C | 200 g | 181 g | 120 min | 19 μm | 68 μm | 150 μm |
| 3D | 200 g | 175 g | 180 min | 13 μm | 48 μm | 109 μm |

Reference Example 1

Dust Explosion Test by Modified Hartmann Apparatus:

This test was performed based on procedures from VDI 2263, Part 1 (Section 2.1.1), "Dust fires and dust explosions; hazards, assessment, protective measures", using a Modified Hartmann Apparatus. Pirfenidone was dried at 50° C. under vacuum, sieved through 63μ sieve. Weighed amount of product was charged into a modified hartmann tube of 1.2 liter volume. The product was converted into a dust cloud in glass cylindrical tube with compressed air and electrodes with continuous spark was used as ignition source to ignite the dust cloud. Based on dust fire or extent of opening of the hinged cover rating 0, 1 or 2 are assigned.

| Observation | Class |
|---|---|
| No fire or explosion | $St_{0H}$ |
| Dust fire or mild explosion | $St_{1H}$ |
| Violent explosion | $St_{2H}$ |

The obtained results are tabulated:

| S. No | Wt. of sample (mg) | Eq. dust concentration (g/m3) | Class |
|---|---|---|---|
| 1 | 120 | 100 | 1 |
| 2 | 240 | 200 | 2 |

Reference Example 2

Shock Sensitive Test by Fall Hammer Test:

This test was performed by Lutoif/ESCIS method using swissi process safety GmbH falling hammer MP03. The hammer (weight 5 kg) was raised and fixed at a height of 80 cm. A Pirfenidone capsule was placed on the lower part of the stamp. The upper stamp was placed on the sample. The hammer was released by using release lever. Result: Detonation was observed (spart and/or smoke/fumes).

Reference Example 3

Minimum Ignition Energy Test by MIKE3:

This test was performed based on international test method VDI 2263 part 1.2.5 using MIKE3. Pirfenidone was dried at 50° C. under vacuum, sieved through 63μ sieve. The product was converted into a dust cloud in glass cylindrical tube with compressed air. The spark for ignition was provided with moving electrodes assembly at different energy levels from 1 mJ to 1000 mJ. The energy just sufficient to ignite the dust under ignition was determined. This ignition energy was then successively halved with variation of the dust concentration and the ignition delay time in a series of tests until no ignition takes place in at least 10 successive experiments. The minimum ignition energy MIE lies between the lowest energy value at which ignition occurred and at the energy value at which no ignition observed for 10 successive experiments. The recommendations for interpreting MIE results are based on energy levels available on MIKE 3 apparatus. According to usual practice, MIE can be ranked as follow:

| Observation | Result |
| --- | --- |
| MIE > 1000 mJ | Sample almost insensitive to electrostatic ignition |
| 300 mJ < MIE < 1000 mJ, 100 mJ < MIE < 300 mJ and 30 mJ < MIE < 100 mJ | Sample sensitive to electrostatic ignition |
| 10 mJ < MIE < 30 mJ and 3 mJ < MIE < 10 mJ | Sample very sensitive to electrostat icignition |
| 1 mJ < MIE < 3 mJ and MIE < 1 mJ | sample extremely sensitive to electrostatic ignition |

Results: 1 mJ<MIE <3 mJ/Es=1.7 mJ.

Reference Example 4

Preparation of Pirfenidone:

A mixture of 5-methyl-1H-pyridin-2-one (100 g), bromo benzene (259 g, comprising greater than 0.2% by weight dibromobenzene isomers) and dimethylformamide (200 ml) were added in to a round bottom flask and stirred up to complete dissolution. Potassium carbonate (254 g) and copper (I) chloride (18.2 g) was added to the above reaction mass and then heated to 130-140° C. The reaction mass was stirred at 130-140° C. for 10 hrs. After the reaction completion, the reaction mass was cooled to 25-35° C. Toluene (500 ml), aqueous sodium chloride (75 g of sodium chloride in 500 ml of water) was added to the reaction mass and stirred for 15-30 mins at 25-35° C. The reaction mass was filtered and the filtrate was allowed to settle. Organic and aqueous layers were separated and the aqueous layer was extracted with toluene. Organic layers combined and was washed with aqueous sodium chloride, treated with carbon and filtered through hyflo. The solvent from the filtrate was distilled off completely under vacuum at below 60° C. Toluene (300 ml) was added to the obtained residue and stirred for 30 mins. The reaction mass was heated to 77-83° C. and stirred for 45 mins. The reaction mass was cooled to 25-35° C. over 60 mins. The reaction mass was further cooled to 0-6° C. The solid obtained was filtered, washed with toluene and dried under vacuum. DM water (500 ml) was added to the above obtained wet compound followed by 50% aqueous sodium hydroxide solution (10 g of sodium hydroxide in 20 ml of water) at 25-35° C. The reaction mass was heated to 75-85° C. and stirred for 30-60 mins. The reaction mass was then gradually cooled to 25-35° C. and stirred for 60 mins. The reaction mass was further cooled to 0-5° C. and stirred for 3 hrs. The obtained solid was filtered, washed with water and dried to provide the title compound.

Reference Example 5

Purification of Pirfenidone

Dissolving crude Pirfenidone (50 g) in ethyl acetate (100 mL) at 65-75° C. and the reaction mass was treated with activated carbon (5 g) and filtered through a short bed of Hyflo. The filtrate was partially concentrated, under reduced pressure while maintain temperature below 60° C. The mixture was gradually allowed to cool to 30±5° C. and then stirred for another 30-60 min. The suspension was again allowed to cool to 0-5° C. and maintained for another 2-3 h, at the same temperature. The precipitated material was filtered and then dried at 60±5° C., for 6-8 h, to afford Pirfenidone as white colored powder (HPLC purity 99.9%; dimer content 0.03%). Yield: 45 g.

Particle size distribution: D10: 1330 µm, D50: 1950 µm, D90: 2840 µm

It will be understood that various modifications may be made to the embodiments disclosed herein. Therefore the above description should not be constructed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the specification appended hereto.

We claim:
1. A process for preparation of pirfenidone of Formula (I),

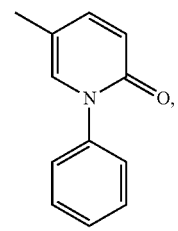

Formula (I)

having a particle size distribution characterized by D90 from 50 microns to 500 microns, comprising:
 a) reacting 5-methyl-1H-pyridin-2-one of Formula (II),

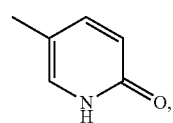

Formula (II)

with bromobenzene of Formula (III),

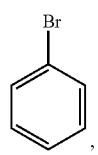

Formula (III)

in the presence of a copper catalyst and a base in an organic solvent to provide pirfenidone, wherein the bromobenzene contains about 0.2% or more by weight of dibromobenzene;

b) isolating the pirfenidone; and c) reducing the particle size of the isolated pirfenidone to arrive at the particle size distribution, wherein the particle size reduction of step c) comprises wet milling the isolated pirfenidone of step b) using one of a colloid mill, ultrasonicator, and high speed homogenizer device, and wherein the size-reduced pirfenidone recovered after the wet milling is characterized by a particle size distribution of D10 greater than about 10 µm and less than about 50 µm, D50 greater than about 35 µm and less than about 150 µm, and D90 greater than about 85 µm and less than about 300 µM.

2. The process of claim 1, wherein the copper catalyst is selected from the group consisting of copper (I) chloride, copper (I) bromide, and copper (I) iodide.

3. The process of claim 1, wherein the base is selected from the group consisting of potassium carbonate, potassium bicarbonate, sodium carbonate, sodium bicarbonate, potassium hydroxide, sodium hydroxide, lithium hydroxide, trimethylamine, and diisopropylethylamine.

4. The process of claim 1, wherein the organic solvent is one or more of a hydrocarbon solvent, an amide solvent, and dimethylsulfoxide.

5. The process of claim 4, wherein the hydrocarbon solvent is selected from the group consisting of benzene, chlorobenzene, toluene, xylene, heptane, hexane, cyclohexane, methyl cyclohexane, or cyclopentane; and the amide solvent is selected from the group consisting of dimethylacetamide, dimethylformamide, N-methylformamdide, dimethylimidazolidinone, and N-methyl pyrrolidinone.

6. The process of claim 1, wherein the copper catalyst is copper (I) chloride, the base is potassium carbonate, and the organic solvent is dimethylformamide.

7. The process of claim 1, further comprising:

d) forming a pharmaceutical composition comprising the pirfenidone from step b) or step c) and at least one pharmaceutically acceptable excipient.

8. A process for the purification of pirfenidone, comprising:

a) treating pirfenidone with an alkaline base selected from sodium hydroxide, potassium hydroxide, sodium carbonate, potassium carbonate, sodium bicarbonate, potassium bicarbonate, and mixtures thereof; and b) isolating a pure pirfenidone, wherein the isolated pirfenidone is characterized by a particle size distribution after wet milling of D10 greater than about 10 µm and less than about 50 µm, D50 greater than about 35 µm and less than about 150 µm, and D90 greater than about 85 µm and less than about 300 µm.

9. The process of claim 8, wherein the alkaline base is aqueous sodium hydroxide.

10. The process of claim 8, wherein isolating the pirfenidone of step b) comprises cooling of the reaction mass from step a) to below about 20° C. followed by filtration.

11. A process for preparation of pirfenidone having a particle size distribution characterized by D90 from 50 microns to 500 microns, comprising:

a) dissolving pirfenidone in an ester solvent selected from the group consisting of ethyl acetate, methyl acetate, isopropyl acetate, and mixtures thereof, or in an aromatic hydrocarbon selected from the group consisting of toluene, xylene, and mixtures thereof;

b) isolating the pirfenidone, wherein the isolated pirfenidone is characterized as having less than 0.1% by HPLC of a dimer impurity of Formula (IV),

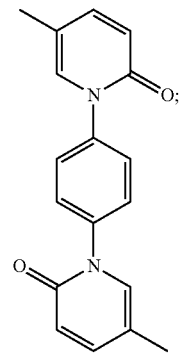

Formula (IV)

and c) reducing the particle size of the isolated pirfenidone to arrive at a size-reduced pirfenidone recovered after wet milling the isolated pirfenidone of step b) using one of a colloid mill, ultrasonicator, and high speed homogenizer device, characterized by a particle size distribution of D10 greater than about 10 µm and less than about 50 µm, D50 greater than about 35 µm and less than about 150 µm, and D90 greater than about 85 µm and less than about 300 µm.

12. The process of claim 11, wherein the ester solvent is ethyl acetate and the aromatic hydrocarbon solvent is toluene.

13. The process of claim 11, wherein isolating the pirfenidone of step b) comprises cooling of the reaction mass from step a) to below about 25° C. followed by filtration.

14. The process of claim 11, further comprising:

d) forming a pharmaceutical composition comprising the pirfenidone from step b) or step c) and at least one pharmaceutically acceptable excipient.

15. A process for preparing pirfenidone having a particle size distribution characterized by D90 from 50 microns to 500 microns comprising:

a) dissolving pirfenidone in an organic solvent selected from one of toluene, isopropyl acetate, methyl acetate, ethyl acetate, methanol, ethanol, isopropanol, n-propanol, acetone, methyl ethyl ketone, methyl isobutyl ketone, methyl tertiary butyl ether, tetrahydrofuran, dimethyl ether, diisopropyl ether, 1,4-dioxane, and mixtures thereof;

b) adding to the above reaction mass of step a) an antisolvent selected from one of water and a hydrocarbon selected from the group consisting of n-pentane, n-hexane, n-heptane, cyclohexane, methyl cyclohexane, cycloheptane, and mixture thereof; and c) isolating the pirfenidone, wherein step c) comprises wet milling the isolated pirfenidone of step b) using one of a colloid mill, ultrasonicator, and high speed homogenizer device, and wherein the size-reduced pirfenidone recovered after the wet milling is characterized by a particle size distribution of D10 greater than about 10 µm and less than about 50 µm, D50 greater than about 35 µm and less than about 150 µm, and D90 greater than about 85 µm and less than about 300 µm.

16. The process of claim 15, wherein the organic solvent is ethyl acetate and the antisolvent is n-heptane.

17. The process of claim 15, wherein the adding step b) comprises:
adding a first amount of the antisolvent at a first temperature of 0 to −10° C. followed by isolation of a first amount of the pirfenidone;
adding a second amount of the antisolvent at a second temperature of 0 to 10° C. followed by isolation of a second amount of the pirfenidone; and
adding a third amount of the antisolvent at a third temperature of below 45° C. followed by isolation of a third amount of the pirfenidone.

18. The process of claim 15, wherein isolating the pirfenidone of step c) comprises optionally cooling of the reaction mass of step b) to below about 30° C. followed by filtration.

19. The process of claim 15, further comprising:
d) forming a pharmaceutical composition comprising the isolated pirfenidone and at least one pharmaceutically acceptable excipient.

20. A process for reducing particle size of pirfenidone comprising:
wet milling of pirfenidone to reduce the particle size of the pirfenidone; and
recovering the pirfenidone,
wherein the size-reduced pirfenidone recovered after the wet milling is characterized by a particle size distribution of D10 greater than about 10 μm and less than about 50 μm, D50 greater than about 35 μm and less than about 150 μm, and D90 greater than about 85 μm and less than about 300 μM.

21. The process of claim 20, wherein the step of wet milling is performed using one of a colloid mill, ultrasonicator, and high speed homogenizer device.

22. The process of claim 20, wherein the step of wet milling is carried out in water.

23. A process for particle size reduction of pirfenidone by wet milling, comprising:
a) mixing pirfenidone in water and wet milling the same in one of a colloid mill, ultrasonicator, and high speed homogenizer device for a period of time and at a sufficient temperature to reduce the particle size of the pirfenidone; and
b) recovering the pirfenidone after the period of time,
wherein the pirfenidone recovered after wet milling is characterized as having a particle size distribution of D10 greater than about 10 μm and less than about 50 μm, D50 greater than about 30 μm and less than about 150 μm, and D90 greater than about 80 μm and less than about 300 μm and one or more of a lower explosive initiation energy, a lower shock sensitivity, and a lower minimum ignition energy, compared to the pirfenidone before the wet milling.

24. A process for particle size reduction of pirfenidone by wet milling, comprising:
a) mixing pirfenidone with water;
b) circulating the step a) mixture in a colloidal mill device at a circulation temperature from about 5° C. to about 65° C. sufficient to reduce the particle size of the pirfenidone; and
c) recovering the pirfenidone,
wherein the recovered pirfenidone exhibits a particle size distribution of D10 greater than about 10 μm and less than about 50 μm, D50 greater than about 30 μm and less than about 150 μm, and D90 greater than about 80 μm and less than about 300 μm, and one or more of a lower explosive initiation energy, a lower shock sensitivity, and a lower minimum ignition energy, compared to the pirfenidone prior to circulating the same in the colloidal mill device.

25. The process of claim 24, wherein the circulating step b) is conducted at 1,000 to 8,000 revolutions per minute.

26. The process of claim 24, wherein the circulation step b) is conducted for a period of time of about 30 minutes to about 24 hours.

27. A process for particle size reduction of pirfenidone, by wet milling, comprising:
a) mixing pirfenidone with water;
b) sonicating the step a) mixture in an ultrasonicator device; and
c) recovering the pirfenidone;
wherein the size-reduced pirfenidone recovered after the wet milling is characterized by a particle size distribution of D10 greater than about 10 μm and less than about 50 μm, D50 greater than about 35 μm and less than about 150 μm, and D90 greater than about 85 μm and less than about 300 μm.

28. The process of claim 27, wherein the sonication step b) is carried out at a temperature of about 25° C. to about 50° C. for a period of about 1 hour to about 5 hours.

29. A process for particle size reduction of pirfenidone by wet milling, comprising:
a) mixing pirfenidone with water in a homogenizer device;
b) stirring the step a) mixture; and
c) recovering the pirfenidone,
wherein the size-reduced pirfenidone recovered after the wet milling is characterized by a particle size distribution of D10 greater than about 10 μm and less than about 50 μm, D50 greater than about 35 μm and less than about 150 μm, and D90 greater than about 85 μm and less than about 300 μM.

30. The process of claim 29, wherein the stirring step b) is carried out at a temperature of about 25° C. to about 50° C. for a period of about 1 hour to about 5 hours.

* * * * *